United States Patent [19]

Vinas

[11] Patent Number: 4,873,223
[45] Date of Patent: Oct. 10, 1989

[54] ZINC SALT OF FRUCTOSE-1,6-DIPHOSPHATE

[75] Inventor: Antonio B. Viñas, Barcelona, Spain

[73] Assignee: Laboratrios Vinas, S.A., Barcelona, Spain

[21] Appl. No.: 838,996

[22] Filed: Mar. 12, 1986

[30] Foreign Application Priority Data

Mar. 15, 1985 [ES] Spain ................................. 541.277

[51] Int. Cl.4 ..................... A61K 31/70; C07H 13/00
[52] U.S. Cl. ..................................... 514/23; 536/115; 536/121
[58] Field of Search ................... 514/23; 536/121, 115

[56] References Cited

U.S. PATENT DOCUMENTS 4,225,592  9/1980  Lakatos et al. ..................... 536/121
4,246,399  1/1981  Higuchi et al. ..................... 536/121
4,448,771  5/1984  Cattani et al. ......................... 536/23

OTHER PUBLICATIONS

The Merck Index 9th ed., 1976, p. 549, Nos. 4123 and 4124.

Primary Examiner—Johnnie R. Brown
Assistant Examiner—Elli Peselev
Attorney, Agent, or Firm—Flynn, Thiel, Boutell & Tanis

[57] ABSTRACT

The zinc salt of fructose-1,6-diphosphate, a pharmaceutical composition including the salt and a method of treating male infertility due to Zn, fructose deficiencies in the seminal plasma or inversion of testicular function due to old age in a patient.

4 Claims, No Drawings

ZINC SALT OF FRUCTOSE-1,6-DIPHOSPHATE

This invention refers to a new derivative of fructose-1,6-diphosphate and, more particularly, to the zinc salt thereof, having the formula

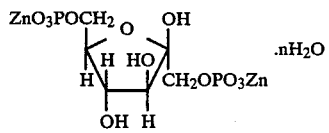

wherein n is an integer of 0 to 4.

This invention has a series of advantages because of the applications which can be derived from the therapeutic viewpoint.

In fact, the compound thus obtained contains in its formula the zinc ($Zn^{+2}$) divalent cation and the fructose-1,6-diphosphate moiety. Therefore the administration of the compound, the zinc salt of fructose-1,6-diphosphate, at dosages which can vary under the medical formulation according to the selected route of administration (oral, parenteral, rectal, etc.) allows animals (experimental pharmacology) or humans to make use of both moieties with their corresponding advantages.

Zinc has therapeutic effects on the gonadal dysfunction. The concentration of zinc in plasma is an important factor in regulating fertility; when the Zn levels in seminal plasma are low, a decrease in the potential fertility in man and secretory male sterility has been observed. The addition of zinc regulates (normalizes) the testosterone in serum and the concentration of the spermatozoa in the ejaculate as well as their motility. For this reason, zinc is believed to be necessary as a favorable medium for the motility and activity of spermatozoa. The bioavailability of zinc has an effect on the activity of some testicular enzymes.

The medical literature contains some cases of idiopathic male infertility, involution of the testicular function with age which were treated successfully with zinc. There are cases of women who become pregnant after the affected men were treated.

In many mammals, including man, seminal plasma contains fructose as a main sugar. In man, seminal fructose is derived mainly from seminal vesicles.

The concentration of fructose in human ejaculate is on the order of 100–500 mg/100 cc. Fructose supplies the energy necessary to the motility of spermatozoa by anaerobic glycolysis. It is the substratum for the metabolism of spermatozoa. After one hour of incubation at 37° C., the mg of fructose used by spermatozoa can be measured, which demonstrates the basic role of this sugar. Ripe human spermatozoa are not active if they cannot use fructose as a main source of energy for producing ATP.

It has been demonstrated that products which produce male infertility, such as chlorohydrins, inhibit the oxidizing metabolism of fructose.

There are deficits of fructose in semen which are associated with certain forms of hypogonadism. Ejaculations in which the seminal plasma has not been recovered enough (24 hours) contain a lesser amount of fructose. The determination of fructose in the ejaculation gives not only a quantitative measurement of the vesicular contribution to the constitution of the ejaculation but also can serve as a useful means for detecting an occlusion in the ejaculation canals.

From the toxicological viewpoint, the fructose derivative, according to the invention, has the advantage, compared to other zinc salts, of its low toxicity when given orally. In a group of 10 rats, a dosage of 4000 mg/kg did not produce any deaths. When given intraperitoneally, the $DL_{50}$ value is between 125 and 150 mg/kg (similar to other zinc salts). This low oral toxicity is related to the slow absorption of this molecule which makes it particularly interesting for its administration by this oral route. It has been verified that the zinc values in plasma start to increase within two hours after administering the compound. Five hours after its administration, the increases are about 40% in the content of $Zn^{2+}$ in plasma.

Due to the pathology to which the product can be applied, higher levels of $Zn^{2+}$ have been found in seminal vesicles and testicles of treated rats compared with control groups.

In the following table, $Zn^{2+}$ levels in ppm compared to the weight of the organ have been indicated. An increase in $Zn^{2+}$ levels can be seen in testicles as in the seminal vesicles. Mean values affected by the mean error are represented.

TABLE

| $Zn^{2+}$ levels (ppm) in rats after oral administration of 150 mg/kg of zinc fructose 1,6-diphosphate. | | |
|---|---|---|
| | Control Group | Treated Group |
| Seminal Vesicles | 500.6 ± 51.2 | 651.2 ± 34.3$^x$ |
| Testicle | 680.8 ± 43.6 | 726 ± 24.4 |

$^x p < 0.05$

The process for preparing the zinc salt of fructose-1,6-diphosphate, according to this invention, comprises reacting fructose-1,6-diphosphate, or its ammonia or alkali metal salt, with an oxide or hydroxide of zinc, or a zinc salt, in a solvent or a mixture of polar solvents, preferably water or methanol. The temperature of the reaction can vary between 0° C. and the boiling point of the solvent. Zinc salt of fructose-1,6-diphosphate is obtained by crystallization in the cold or by removing the solvent.

Following are some examples of the reaction for preparing the invention compound. The examples are given as illustrations, but not as limiting the scope of the invention.

EXAMPLE 1

In a 250 ml flask, 8.98 g of fructose-1,6-disodium diphosphate were dissolved in 40 ml water. While stirring, a previously prepared solution of 8.78 g of zinc acetate monohydrate in 100 ml water was added at a temperature of 60° C. The mixture was stirred for one hour, cooled, and kept overnight at 5° C. A crystalline precipitate was produced, which was then filtered, washed with cold water and dried in a desiccator. 7.15 g of the product was thus obtained. The collected liquid residue was treated with acetone and a new precipitate was produced which was treated the same way as described above. An additional 2.04 g of the product was thus obtained.

Melting point >300° C.
Elemental analysis:
Calculated for $C_6H_{14}O_{14}P_2Zn_2$: % C 14.33; % H 2.81; % Zn 26.00.
Found: % C 14.03; % H 2.67; % Zn 26.0.

The IR spectrum is similar to that of the fructose-1,6-disodium-diphosphate.

EXAMPLE 2

In a 250 ml flask, 8.98 g fructose-1,6-disodium diphosphate was dissolved in 140 ml water. While stirring, 4.39 g zinc basic carbonate was added, at 60° C., and the mixture is stirred for one hour, thus obtaining a solution which was treated as in the previous example. 9.30 g of the product having characteristics similar to those of the product of Example 1 were obtained.

Accordingly, the zinc salt of fructose-1,6-diphosphate, according to the present invention, is useful as an excellent agent for treating a condition of low zinc concentration and/or low fructose concentration in seminal plasma, caused by gonadal dysfunction, etc.

The dose of the zinc salt of fructose-1,6-diphosphate of the present invention as an agent for treating the effects of gonadal dysfunction depends on various factors such as the severity of the condition of the patient. It may be usually administered to an adult orally or parenterally in a dose of 10 to 500 mg once to four times a day without any limitation.

It may be formulated into various forms such as powders, grains, granules, tablets, capsules and injections. Formulation may be carried out in a conventional manner with the use of conventional carriers.

I claim:

1. Zinc salt of fructose-1,6-diphosphate having the formula

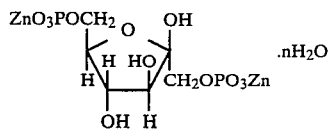

wherein n = 0 to 4.

2. A pharmaceutical composition comprising a therapeutically effective amount of the compound as claimed in claim 1, in combination with a pharmacologically acceptable carrier for treating a condition of low zinc concentration or low fructose concentration in seminal plasma caused by gonadal dysfunction, in males.

3. A method of treating a male patient suffering from a condition of low zinc concentration or low fructose concentration in seminal plasma caused by gonadal dysfunction, which comprises administering to such a patient a therapeutically effective amount of a pharmaceutical composition comprising a therapeutically effective amount of the zinc salt of fructose-1,6-diphosphate having the formula

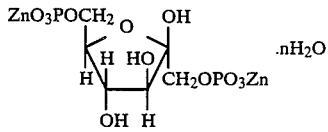

wherein n=0 to 4, in combination with a pharmacologically acceptable carrier.

4. A method as claimed in claim 3, in which from 10 to 500 mg of said zinc salt of fructose-1,6-diphosphate is administered orally or parenterally from 1 to 4 times a day.

* * * * *